US006653382B1

(12) United States Patent
Statz et al.

(10) Patent No.: US 6,653,382 B1
(45) Date of Patent: *Nov. 25, 2003

(54) HIGHLY-NEUTRALIZED ETHYLENE COPOLYMERS AND THEIR USE IN GOLF BALLS

(75) Inventors: Robert Joseph Statz, Kennett Square, PA (US); John Chu Chen, Hockessin, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 09/691,284

(22) Filed: Oct. 18, 2000

Related U.S. Application Data

(63) Continuation-in-part of application No. 09/558,894, filed on Apr. 27, 2000, which is a continuation-in-part of application No. 09/422,142, filed on Oct. 21, 1999, now abandoned.

(51) Int. Cl.$^7$ ............................ C08K 5/09; A63B 37/12
(52) U.S. Cl. ................. 524/400; 524/394; 524/397; 525/330.2; 473/372; 473/373; 473/385
(58) Field of Search ................. 524/394, 397, 524/400; 525/330.2; 473/372, 373, 385

(56) References Cited

U.S. PATENT DOCUMENTS

| 3,384,612 A | | 5/1968 | Brandt et al. |
| 3,404,134 A | * | 10/1968 | Rees |
| 3,649,578 A | * | 3/1972 | Bush |
| 4,911,451 A | | 3/1990 | Sullivan et al. |
| 5,155,157 A | | 10/1992 | Statz et al. |
| 5,306,760 A | | 4/1994 | Sullivan |
| 5,312,857 A | | 5/1994 | Sullivan |
| 5,688,869 A | * | 11/1997 | Sullivan |
| 5,691,418 A | | 11/1997 | Hagman et al. |
| 5,895,105 A | * | 4/1999 | Nesbitt |
| 5,902,855 A | | 5/1999 | Sullivan |
| 5,973,046 A | | 10/1999 | Chen et al. |

FOREIGN PATENT DOCUMENTS

| BE | 699171 | 11/1967 |
| EP | 0 339 743 | 11/1989 |
| GB | 2 164 342 | 3/1986 |
| GB | 2 168 059 | 6/1986 |
| WO | WO 92/12206 | 7/1992 |
| WO | WO 98/03565 | 1/1998 |
| WO | WO 98 46671 | 10/1998 |
| WO | WO 00 23519 | 4/2000 |

OTHER PUBLICATIONS

PCT International Search Report for International application No. PCT/US00/28822, dated Jan. 16, 2001.
PCT International Search Report for International application No. PCT/US99/24700.
Ionomeric polyblends based on zinc salts for maleated ethylene–propylene diene monomer and maleated high density polyethylene, *Plastics Rubber and Composites Processing and Applications*, vol. 26, No. 7, pp. 311–317, 1997.

* cited by examiner

*Primary Examiner*—David J. Buttner

(57) ABSTRACT

Thermoplastics with high resilience (high coefficient of restitution) and softness (low Atti compressions) and their use in golf ball components. Melt-processable, highly-neutralized ethylene acid copolymers and process for making them by incorporating an aliphatic, mono-functional organic acid in the acid copolymer and then neutralizing greater than 90% of all the acid groups present.

22 Claims, No Drawings

HIGHLY-NEUTRALIZED ETHYLENE COPOLYMERS AND THEIR USE IN GOLF BALLS

This application is a continuation-in-part of U.S. patent application Ser. No. 09/558,894 filed Apr. 27, 2000, which claims priority and is a cip to U.S. patent application Ser. No. 09/422,142 filed Oct. 21, 1999 now abandoned.

BACKGROUND OF THE INVENTION

1. Field of the Invention

The invention relates to melt-processible, highly-neutralized ethylene, $C_3$ to $C_8$ $\alpha,\beta$ ethylenically unsaturated carboxylic acid copolymers and process for making them. It relates to such copolymers, neutralized to greater than 90%, particularly to those neutralized to nearly to or to 100%. These copolymers are made by incorporating a sufficient amount of specific organic acid (or salt) into the copolymer before neutralization to the high level.

The invention particularly relates to melt-processible, highly-neutralized (greater than 90%) polymer comprising (1) ethylene, $C_3$ to $C_8$ $\alpha,\beta$ ethylenically unsaturated carboxylic acid copolymers that have their crystallinity disrupted by addition of a softening monomer or other means, and (2) sufficient amount of a non-volatile, non-migratory agent such as an organic acid (or salt) selected for its ability to substantially or totally suppress the ethylene crystallinity. Agents other than organic acids (or salts) may be used.

The invention also relates to thermoplastics that, when molded into spheres, have a coefficient of restitution of at least 0.785 (measured by firing a sphere of the thermoplastic at an initial velocity of 125 feet/second against a steel wall positioned 3 feet from the point where initial velocity and rebound velocity are determined and by dividing the rebound velocity by the initial velocity) and an Atti compression of no more than 100.

These copolymers are useful in making molded products such as golf ball components, thermoplastic shoe soles for cleated footwear, and resilient foams for sporting goods. They are particularly useful in the manufacture of one-, two-, and three-piece and multi-layered golf balls. The invention particularly relates to the spherical components (cores, centers, and one-piece balls) having a coefficient of restitution of at least 0.785 when measured at 125 feet/second and Atti compressions of 100 or less.

2. Description of Related Art

Typical premium golf balls include three-piece balls, two-piece balls and multi-layered balls. "Three-piece" balls typically have a spherical molded center, elastomeric thread-like material wound around the center, and either a thermoplastic or thermoset cover. "Two-piece" balls typically have a spherical molded core covered with a thermoplastic material. "Multi-layered" balls typically have a spherical molded core and one or more intermediate layers or mantles between the core and a cover.

Three-piece centers and two-piece and multi-layer-cores have traditionally been made using a thermoset rubber such as polybutadiene rubber. With thermoset rubber, complex multi-step processes are needed to make cores and centers and scrap cannot be recycled. Attempts to solve these difficulties by substituting a thermoplastic for the thermoset have had limited success. Also, attempts to make premium one-piece balls have been unsuccessful. See U.S. Pat. No. 5,155,157, UK Patent Application 2,164,342A and WO 92/12206. Balls, cores and centers made based on these references have a high cost and lack properties such as durability, softness (low Atti compression), and resilience to make them useful in premium balls.

One thermoplastic that has found utility in golf ball components and other applications for a long time are ionomers of copolymers of alpha olefins, particularly ethylene, and $C_{3-8}$ $\alpha,\beta$ ethylenically unsaturated carboxylic acid. U.S. Pat. No. 3,264,272 (Rees) teaches methods for making such ionomers from "direct" acid copolymers. "Direct" copolymers are polymers polymerized by adding all monomers simultaneously, as distinct from a graft copolymer, where another monomer is grafted onto an existing polymer, often by a subsequent free radical reaction. A process for preparing the acid copolymers on which the ionomers are based is described in U.S. Pat. No. 4,351,931.

The acid copolymers may contain a third "softening" monomer that disrupts the crystallinity of the polymer. These acid copolymers, when the alpha olefin is ethylene, can be described as an E/X/Y copolymers wherein E is ethylene, X is the $\alpha,\beta$ ethylenically unsaturated carboxylic acid, particularly acylic and methacrylic acid, and Y is the softening co-monomer. Preferred softening co-monomers are $C_1$ to $C_8$ alkyl acrylate or methacrylate esters. X and Y can be present in a wide range of percentages, X typically up to about 35 weight percent (wt. %) of the polymer and Y typically up to about 50 weight percent of the polymer.

A wide range of cations is known for neutralizing acid moieties in the acid copolymer. The degree of neutralization is known to vary over a wide range. Typical cations include lithium, sodium, potassium, magnesium, calcium, barium, lead, tin, zinc, aluminum, and combinations of such cations. Neutralization to 90% and higher, including up to 100%, is known, but such a high degree of neutralization results in a loss of melt-processibility or properties such as elongation and toughness. This is particularly so for copolymers with high acid levels and when using cations other than barium, lead and tin to neutralize the copolymer.

SUMMARY OF THE INVENTION

The thermoplastic composition of this invention comprises a polymer which, when formed into a sphere that is 1.50 to 1.54 inches in diameter, has a coefficient of restitution (COR) when measured by firing the sphere at an initial velocity of 125 feet/second against a steel plate positioned 3 feet from the point where initial velocity and rebound velocity are determined and by dividing the rebound velocity from the plate by the initial velocity and an Atti compression of no more than 100.

The thermoplastic composition of this invention preferably comprises (a) aliphatic, mono-functional organic acid(s) having fewer than 36 carbon atoms; and (b) ethylene, $C_3$ to $C_8$ $\alpha,\beta$ ethylenically unsaturated carboxylic acid copolymer(s) and ionomer(s) thereof, wherein greater than 90%, preferably near 100%, and more preferably 100% of all the acid of (a) and (b) are neutralized.

The thermopastic composition preferably comprises melt-processible, highly-neutralized (greater than 90%, preferably near 100%, and more preferably 100%) polymer of (1) ethylene, $C_3$ to $C_8$ $\alpha,\beta$ ethylenically unsaturated carboxylic acid copolymers that have their crystallinity disrupted by addition of a softening monomer or other means such as high acid levels, and (2) non-volatile, non-migratory agents such as organic acids (or salts) selected for their ability to substantially or totally suppress any remaining ethylene crystallinity. Agents other than organic acids (or salts) may be used.

It has been found that, by modifying an acid copolymer or ionomer with a sufficient amount of specific organic acids (or salts thereof); it is possible to highly neutralize the acid copolymer without losing processability or properties such as elongation and toughness. The organic acids employed in the present invention are aliphatic, mono-functional, saturated or unsaturated organic acids, particularly those having fewer than 36 carbon atoms, and particularly those that are non-volatile and non-migratory and exhibit ionic array plasticizing and ethylene crystallinity suppression properties.

With the addition of sufficient organic acid, greater than 90%, nearly 100%, and preferably 100% of the acid moieties in the acid copolymer from which the ionomer is made can be neutralized without losing the processability and properties of elongation and toughness.

The melt-processible, highly-neutralized acid copolymer ionomer can be produced by (a) melt-blending (1) ethylene $\alpha,\beta$ ethylenically unsaturated $C_{3-8}$ carboxylic acid copolymer(s) or melt-processible ionomer(s) thereof (ionomers that are not neutralized to the level that they have become intractable, that is not melt-processible) with (1) one or more aliphatic, mono-functional, saturated or unsaturated organic acids having fewer than 36 carbon atoms or salts of the organic acids, and then concurrently or subsequently (b) Adding a sufficient amount of a cation source to increase the level of neutralization all the acid moieties (including those in the acid copolymer and in the organic acid) to greater than 90%, preferably near 100%, more preferably to 100%.

Preferably, highly-neutralized thermoplastics of this invention can be produced by (a) melt-blending (1) ethylene, $\alpha,\beta$ ethylenically unsaturated $C_{3-8}$ carboxylic acid copolymer(s) or melt-processible ionomer(s) thereof that have their crystallinity disrupted by addition of a softening monomer or other means with (2) sufficient non-volatile, non-migratory agents to substantially remove the remaining ethylene crystallinity, and then concurrently or subsequently (b) Adding a sufficient amount of a cation source to increase the level of neutralization all the acid moieties (including those in the acid copolymer and in the organic acid if the non-volatile, non-migratory agent is an organic acid) to greater than 90%, preferably near 100%, more preferably to 100%.

DETAILED DESCRIPTION OF THE INVENTION

In this disclosure, the term "copolymer" is used to refer to polymers containing two or more monomers. The phrase "copolymer of various monomers" means a copolymer whose units are derived from the various monomers. "Consisting essentially of" means that the recited components are essential, while smaller amounts of other components may be present to the extent that they do not detract from the operability of the present invention. The term "(meth)acrylic acid" means methacrylic acid and/or acrylic acid. Likewise, the term "(meth)acrylate" means methacrylate and/or acrylate.

All references identified throughout this Specification including those in the Description of Related Art and those to which this case claims priority are incorporated by reference as if fully set forth herein.

Acid Copolymers

The acid copolymers used in the present invention to make the ionomers are preferably 'direct' acid copolymers. They are preferably alpha olefin, particularly ethylene, $C_{3-8}$ $\alpha,\beta$ ethylenically unsaturated carboxylic acid, particularly acrylic and methacrylic acid, copolymers. They may optionally contain a third softening monomer. By "softening", it is meant that the crystallinity is disrupted (the polymer is made less crystalline). Suitable "softening" comonomers are monomers selected from alkyl acrylate, and alkyl methacrylate, wherein the alkyl groups have from 1–8 carbon atoms.

The acid copolymers, when the alpha olefin is ethylene, can be described as E/X/Y copolymers where E is ethylene, X is the $\alpha,\beta$ ethylenically unsaturated carboxylic acid, and Y is a softening comonomer. X is preferably present in 3–30 (preferably 4–25, most preferably 5–20) wt. % of the polymer, and Y is preferably present in 0–30 (alternatively 3–25 or 10–23) wt. % of the polymer.

The ethylene-acid copolymers with high levels of acid (X) are difficult to prepare in continuous polymerizers because of monomer-polymer phase separation. This difficulty can be avoided however by use of "co-solvent technology" as described in U.S. Pat. No. 5,028,674 or by employing somewhat higher pressures than those at which copolymers with lower acid can be prepared.

Specific acid-copolymers include ethylene/(meth)acrylic acid copolymers. They also include ethylene/(meth)acrylic acid/n-butyl(meth)acrylate, ethylene/(meth)acrylic acid/iso-butyl(meth)acrylate, ethylene/(meth)acrylic acid/methyl (meth)acrylate, and ethylene/(meth)acrylic acid/ethyl(meth) acrylate terpolymers.

Ionomer

The unmodified, melt processable ionomers used in this invention are prepared from acid copolymers as described above under the heading "Acid Copolymers by methods known in the art of preparing ionomers (see Description of Related Art). They include partially neutralized acid copolymers, particularly ethylene/(meth)acrylic acid copolymers. The unmodified ionomers may be neutralized to any level that does not result in an intractable (not melt processible) polymer that does not have useful physical properties. Preferably, about 15 to about 80%, preferably about 50 to about 75% of the acid moiety of the acid copolymer is neutralized by an alkali metal or an alkaline earth metal cation. For acid copolymers having a high acid level (for example over 15 wt. %), the percent neutralization must be lower to retain melt processibility.

Cations useful in making the unmodified ionomers are lithium, sodium, potassium, magnesium, calcium, or zinc, or a combination of such cations.

Organic Acids and Salts

The organic acids employed in the present invention are aliphatic, mono-functional (saturated, unsaturated, or multi-unsaturated) organic acids, particularly those having fewer than 36 carbon atoms. Also salts of these organic acids may be employed. The salts may be any of a wide variety, particularly including the barium, lithium, sodium, zinc, bismuth, potassium, strontium, magnesium or calcium salts of the organic acids.

While it may be useful for the organic acids (and salts) to have a low volatility when being melt-blended with acid copolymer or ionomer, volatility has been found to not be limiting when neutralizing the blend to high levels, particularly near to or at 100%. At 100% neutralization (all acid in copolymer and organic acid neutralized), volatility simply is no longer an issue. As such, organic acids with lower carbon content can be used. It is preferred, however, that the organic acid (or salt) be non-volatile and non-migratory. It is preferred that they are agents that effectively plasticize ionic arrays and/or remove ethylene crystallinity from an ethylene, $C_{3-8}$ α,β ethylenically unsaturated carboxylic acid copolymers or ionomers thereof. By non-volatile, it is meant that they do not volatilize at temperatures of melt blending with the agent with the acid copolymer. By non-migratory, it is meant that the agent does not bloom to the surface of the polymer under normal storage conditions (ambient temperatures. Particularly useful organic acids include $C_4$ to less than $C_{36}$ (say $C_{34}$), $C_6$ to $C_{26}$, particularly $C_6$ to $C_{18}$, particularly $C_6$ to $C_{12}$, organic acids. Particular organic acids useful in the present invention include caproic acid, caprylic acid, capric acid, lauric acid, stearic acid, behenic acid, erucic acid, oleic acid, and linoelic acid.

Filler

The optional filler component of the subject invention is chosen to impart additional density to blends of the previously described components, the selection being dependent upon the type of golf ball desired (i.e., one-piece, two-piece, three-piece or intermediate layer), as will be more fully detailed below. Generally, the filler will be inorganic having a density greater than about 4 grams/cubic centimeter (gm/cc), preferably greater than 5 gm/cc, and will be present in amounts between 0 and about 60 wt. % based on the total weight of the composition. Examples of useful fillers include zinc oxide, barium sulfate, lead silicate and tungsten carbide, tin oxide, as well as the other well known corresponding salts and oxides thereof. It is preferred that the filler materials be non-reactive or almost non-reactive and not stiffen or raise the compression nor reduce the coefficient of restitution significantly.

Other Components

Additional optional additives useful in the practice of the subject invention include acid copolymer wax (e.g., Allied wax AC143 believed to be an ethylene/16–18% acrylic acid copolymer with a number average molecular weight of 2,040) which assist in preventing reaction between the filler materials (e.g., ZnO) and the acid moiety in the ethylene copolymer. Other optional additives include $TiO_2$, which is used as a whitening agent; optical brighteners; surfactants; processing aids; etc.

Soft, High COR Thermoplastic

The present invention relates to a thermoplastic polymer that is soft and resilient ("Soft, High COR Thermoplastic"). This Soft, High COR Thermoplastic, when formed into a sphere that is 1.50 to 1.54 inches in diameter, has a coefficient of restitution of at least 0.785 measured by firing the sphere at an initial velocity of 125 feet/second against a steel plate positioned 3 feet from the point where initial velocity is determined and dividing the velocity of rebound from the plate by the initial velocity and an Atti compression of no more than 100. The invention further pertains to Soft, High COR Thermoplastics with COR's of 0.790, 0.795, 0.800, 0.805, 0.810, 0.815, 0.820, 0.825, 0.830, 0.835, and greater at Atti compressions of 95, 90, 85, 80, 75 and lower.

These Soft, High COR Thermoplastics preferably are compositions that are melt blended polymers of (a) the acid copolymers or the melt processible ionomers as described above and (b) one or more aliphatic, mono-functional organic acids or salts thereof as described above, wherein greater than 90% of all the acid of (a) and of (b) is neutralized. Preferably, nearly 100% of all the acid or 100% of all the acid of (a) and (b) is neutralized by a cation source. Preferably, an amount of cation source in excess of the amount required to neutralize 100% of the acid in (a) and (b) is used to neutralize the acid in (a) and (b).

Preferably, the acid copolymers are E/X/Y copolymers where E is ethylene, X is the α,β ethylenically unsaturated carboxylic acid, and Y is a softening comonomer. X is preferably present in 3–30 (preferably 4–25, most preferably 5–20) wt. % of the polymer, and Y is preferably present in 0–30 (alternatively 3–25 or 10–23) wt. % of the polymer. The organic acid preferably is one that is non-volatile, non-migratory and effectively plasticizes ionic arrays and/or suppresses crystallinity in the E/X/Y copolymer or ionomer.

Preferably the crystallinity of the acid copolymer is disrupted by inclusion of a softening monomer or other means. Other means for disrupting crystallinity include employing high acid levels when there is no softening monomer used can. For example, in E/X/Y copolymers, X can be methacrylic acid present at greater than 18 wt. % or acrylic acid present at greater than 15 wt. % when Y is not present. Preferably, organic acid is selected to substantially or totally suppress the ethylene crystallinity is melt blended with this disrupted crystallinity acid copolymer and then highly neutralized (90% or greater, nearly 100%, 100% of all acid).

Selection of Materials for Resilience and Compression

The specific combinations of resilience and compression used in the practice of the subject invention will in large part be dependent upon the type of golf ball desired (i.e., one-piece, two-piece, three-piece, or multi-layered), and in the type of performance desired for the resulting golf ball as detailed below.

Three-piece Golf Ball Preferred Embodiments

Three-piece balls are manufactured by well known techniques as described in, e.g., U.S. Pat. No. 4,846,910. For purposes of this invention, the center of these three-piece balls is made by injection or compression molding a sphere of desired size from the Soft, High COR Thermoplastic described above that is filled with sufficient filler to provide a center density of from about 1.6 gm/cc to about 1.9 gm/cc depending on the diameter of the center, the windings, and the thickness and composition of the cover to produce a golf ball meeting the weight limits (45 grams) set by the PGA.

Two-piece Golf Ball Preferred Embodiments

Two-piece balls are manufactured by well-known techniques wherein covers are injection or compression molded over cores. For purposes of this invention, the core of these two-piece balls is made by injection or compression molding a sphere of desired size from the Soft, High COR Thermoplastic described above that is filled with sufficient filler to provide a core density of from about 1.14 gm/cc to about 1.2 gm/cc depending on the diameter of the core and the thickness and composition of the cover to produce a golf ball meeting the weight limits (45 grams) set by the PGA.

Multi-Layer Golf Ball Preferred Embodiments

Multi-layer balls are manufactured by well-known techniques wherein an injection or compression molded core is covered by one or more intermediate layers or mantles and an outer cover by injection or compression molding. The core and/or the mantle(s) are made by injection or compression molding a sphere or layer of desired size or thickness from the Soft, High COR Thermoplastic described above which is filled with sufficient filler to provide a golf ball meeting the weight limits (45 grams) set by the PGA. The amount of filler employed in the core and mantle(s) can be varied from 0 to about 60 wt. % depending on the size (thickness) of the components and the desired location of the weight in the ball, provided that the final ball meets the required weight limits. The filler can be used in the core and not in the mantle, in the mantle and not in the core, or in both. While not intending to be limiting as to possible combinations, this embodiment includes:

1. a core comprising the same composition used in the three-piece center with a mantle made of any composition known in the art,
2. a core comprising the same composition used in the two-piece core or three-piece center with a mantle made of the composition of this invention with or without filler. adjusted to provide a golf ball of the desired weight,
3. a core made of any composition (including thermoset compositions such as polybutadiene rubber) with a mantle made of the composition of this invention with or without filler provided that the weight of the finished golf ball meets the required limit.

Covers

Covers for golf balls comprising the Soft, High COR Thermoplastic described above are included in the invention. The covers can be made by injection or compression molding the Soft, High COR Thermoplastic described above (with or without filler, other components, and other thermoplastics including other ionomers) over a thermoplastic or thermoset core of a two-piece golf ball, over windings around a thermoplastic or thermoset center, or as the outer layer of a multi-layer golf ball.

One-piece Golf Ball Preferred Embodiments

One-piece balls can be made by well-known injection or compression techniques. They will have a traditional dimple pattern and may be coated with a urethane lacquer or be painted for appearance purposes, but such a coating and/or painting will not affect the performance characteristics of the ball.

The one-piece ball of this invention is made by injection or compression molding a sphere of desired size from the Soft, High COR Thermoplastic described above that is filled with sufficient filler to provide a golf ball meeting the weight limits (45 grams) set by the PGA. Preferably, enough filler is used so that the ball has a density 1.14 gm/cc.

Process for Making Highly-Neutralized Ionomer

The melt-processible, highly-neutralized acid copolymer ionomer of the present invention can be produced by (a) Melt-blending ethylene α,β ethylenically unsaturated $C_{3-8}$ carboxylic acid copolymer(s) or ionomer(s) thereof that are not neutralized to the level that they have become intractable (not melt-processible) with one or more aliphatic, mono-functional, saturated or unsaturated organic acids having less than 36 carbon atoms or salts of the organic acids, and concurrently of subsequently (b) Adding a sufficient amount of a cation source to increase the level of neutralization all the acid moieties (including those in the acid copolymer and in the organic acid) to greater than 90%, preferably near 100%, more preferably to 100%.

Preferably the aliphatic, mono-functional, saturated or unsaturated organic acids having less than 36 carbon atoms or salts of the organic acids are present in a range of about 5 to about 150 parts (alternatively, about 25 to about 80) per hundred parts (pph) by weight of the ethylene α,β ethylenically unsaturated $C_{3-8}$ carboxylic acid copolymer(s) or ionomer(s) thereof.

Neutralization of acid copolymers and organic acids in this manner (concurrently or subsequently) has been found to be the only way without the use of an inert diluent to neutralize the copolymer without loss of processibility or properties such as toughness and elongation to a level higher than that which would result in loss of melt processibility and properties for the ionomer alone. For example, an acid copolymer can be neutralized to over 90%, preferably to about 100% or to 100% neutralization without losing the melt processibility associated with acid copolymers neutralized to greater than 90%. In addition, neutralizing to about 100% or to 100% reduces the deposits of the organic acids on the mold vent observed upon molding mixtures with less than 100% neutralization.

The acid copolymer(s) or unmodified, melt-processible ionomer(s) can be melt-blended with the organic acid(s) or salt(s) is any manner known in the art. For example, a salt and pepper blend of the components can be made and the components can then be melt-blended in an extruder.

The still melt-processible, acid-copolymer/organic-acid-or-salt blend can be neutralized or further neutralized by methods known in the art. For example, a Werner & Pfleiderer twin screw extruder can be used to neutralize the acid copolymer and the organic acid at the same time.

Depending on the acid level of the co- or ter-polymer, the level of organic acid that controls processablity can be determine based on the disclosures herein. The percent organic acid needs to be higher for higher acid levels in the backbone of co- or terpolymer. See for example the following table (Table 1) comparing melt indices obtained for various acid levels in an E/14–16% nBA/AA terpolymer. Less of a lower molecular weight organic acid is needed to have the same effect as a higher amount of a higher molecular weight organic acid.

A process to make highly-neutralized, melt-processible ionomer comprises the steps of (a) Melt-blending (1) an ethylene α,β ethylenically unsaturated carboxylic acid copolymer or a melt-processible ionomer thereof in which the acid copolymer's ethylene crystallinity has been disrupted; and (2) sufficient non-volatile, non-migratory agent to substantially or totally suppress the remaining ethylene crystallinity of the ethylene α,β ethylenically unsaturated carboxylic acid copolymer or a melt-processible ionomer thereof, and (b) Concurrently or subsequently adding sufficient cation source to neutralize more than 90% (preferably near 100% or at least 100%) of all the acid moieties of the acid copolymer or ionomer thereof and, to the extent that the non-volatile, non-migratory agent contains acid moieties, the acid moieties of the non-volatile, non-migratory agent.

Preferably the non-volatile, non-migratory agent is present in a range of about 5 to about 150 (alternatively, about 25 to about 80) pph by weight of the ethylene α,β ethylenically unsaturated $C_{3-8}$ carboxylic acid copolymer(s) or ionomer(s) thereof.

Preferably, the amount of cation source is in excess of the amount that is required to neutralize all the acid moieties in the acid copolymer or ionomer thereof and, to the extent that the non-volatile, non-migratory agent contains acid moieties, the acid moieties of the non-volatile, non-migratory agent.

Preferably, the process employs an ethylene α,β ethylenically unsaturated carboxylic acid copolymer or a melt-processible ionomer thereof that is an E/X/Y copolymer or melt-processible ionomer of the E/X/Y copolymer where E is ethylene, X is a $C_3$ to $C_8$ α,β ethylenically unsaturated carboxylic acid, and Y is a softening comonomer wherein X is about 4–25 wt. % of the E/X/Y copolymer and Y is about 3–25 wt. % of the E/X/Y copolymer.

Preferably the non-volatile, non-migratory agent is an organic acid or salt, more preferably oleic acid.

TABLE 1

Comparing M.I. To Stearic Acid Level and % AA

| Acid Level | M.I. Base Resin | Stearic Acid Level | | | | |
|---|---|---|---|---|---|---|
| | | 20% | 30% | 35% | 40% | 45% |
| 8.1% AA | 67.9 | | | 1.8 | 2 | 6 |
| About 8.3% AA | 62.5 | | | 1.08 | 1.13 | 2.25 |
| 10.1% AA | 66.8 | | | 0.62 | 1.55 | 2.22 |
| About 6.8% AA | 75 | 1.25 | 1.92 | | 6.52 | |
| About 4.9% AA | 86 | 4.9 | 9.7 | | 23.2 | |

Thermoplastic
Highly-Neutralized, Melt-Processible Ionomer

The resulting thermoplastic composition of this invention consists essentially of (a) aliphatic, mono-functional organic acid(s) having fewer than 36 carbon atoms; and (b) ethylene, $C_3$ to $C_8$ α,β ethylenically unsaturated carboxylic acid copolymer(s) and ionomer(s) thereof, wherein greater than 90%, preferably near 100%, and more preferably 100% of all the acid of (a) and (b) are neutralized.

This resulting highly neutralized; melt-processible acid copolymer of this invention can be melt-blended with other components to produce end products. For example, it may be melt-blended with components employed in co-pending U.S. application Ser. No. 09/422,142 to make one-, two-, three-piece, and multi-layered golf balls and foamed materials useful in footwear and other sport balls such as softballs. The components used with the resulting highly neutralized, melt-processible acid copolymer in this case include thermoplastic polymer components selected from copolyetheresters, copolyetheramides, elastomeric polyolefins, styrene diene block copolymers and thermoplastic polyurethanes; and fillers.

Testing Criteria for Examples

Coefficient of Restitution (COR) is measured by firing an injection-molded neat sphere of the resin having the size of a golf ball from an air cannon at a velocity determined by the air pressure. The initial velocity generally employed is 125 feet/second. The sphere strikes a steel plate positioned three feet away from the point where initial velocity is determined, and rebounds through a speed-monitoring device located at the same point as the initial velocity measurement. The return velocity divided by the initial velocity is the COR.

PGA Compression is defined as the resistance to deformation of a golf ball, measured using an Atti machine.

Tensile properties (tensile at break, elongation at break, tensile yield, and elongation yield) are determined in accord with ASTM D1708.

Percent rebound is determined by dropping the ball (or three-piece center/two-piece core) from a height of 100 inches and measuring the rebound from a hard, rigid surface such as a thick steel plate or a stone block. An acceptable result is about 65–85%.

EXAMPLES

Numbers in parentheses in the tables represent the weight percentage of the component in the blend.

Employing a Werner & Pfleiderer twin screw extruder, 4812 grams of stearic acid were added to 7218 grams of an E/23nBA/9.6MAA polymer. Enough magnesium hydroxide was added to this mixture to neutralize 90% and more than 95% of the available acid. (See Ex 1a & 1b in Table 1).

Two other resins with the composition cited in Table 2 were reacted with stearic acid and magnesium hydroxide. However, in this case, enough magnesium hydroxide was added to neutralize 100% of the available combined acids. These mixed anionic ionomers Ex 1c and 1d are listed in Table 2.

TABLE 2

Magnesium Stearate Modified Magnesium Ionomers

| Ex No | Resin Comp. | Cation Type | Organic Acid (%) | % Neut | M.I. (g/10 min) |
|---|---|---|---|---|---|
| 1a | E/23nBA/9.6MAA | Mg | Stearic(40) | 90 | 5.2 |
| 1b | E/23nBA/9.6MAA | Mg | Stearic(40) | 95 | 3.6 |
| 1c | E/15nBA/8.5AA | Mg | Stearic(40) | >100 | 1.15 |
| 1d | E/16nBA/12AA | Mg | Stearic(40) | >100 | 0.09 |

Properties of the 100% neutralized resin of Example 1c are set forth in the following Table 3.

TABLE 3

| PGA Comp. | COR | Tensile at Break (psi) | Tensile Yield (psi) | Elongation at Break (%) | Elongation Yield (%) |
|---|---|---|---|---|---|
| 90 | .787 | 2802 | 2069 | 340 | 28 |

Thermoplastic Spheres

The following examples describe the preparation of blends for spheres for testing. Extrusion conditions for making blends identified in Table 5 are shown in Tables 4.

TABLE 4

Extrusion Conditions for Making Blends (Table 5)

| Screw Speed Rpm | Zone 1 Temp ° C. | Zone 2–3 Temp ° C. | Zone 4–9 Temp ° C. | Die Temp ° C. | Rate lb./hr | Vac. inches |
|---|---|---|---|---|---|---|
| 100–300 | 75–100 | 125–150 | 140–240 | 200–230 | 15–25 | 28 |

TABLE 5

| Sample | Resin Type (%) | Acid Type (%) | Cation (% neut*.) | M.I. g/10 min |
|---|---|---|---|---|
| 1A | A(60) | OLEIC(40) | Mg(100) | 1.0 |
| 2B | A(60) | OLEIC(40) | Mg(105)* | 0.9 |
| 3C | B(60) | OLEIC(40) | Mg(100) | 0.9 |
| 4D | B(60) | OLEIC(40) | Mg(105)* | 0.9 |
| 5E | B(60) | STEARIC(40) | Mg(100) | 0.85 |

A—ethylene, 14.8% normal butyl acrylate, 8.3% acrylic acid
B—ethylene, 14.9% normal butyl acrylate, 10.1% acrylic acid
*indicates that cation was sufficient to neutralize 105% of all the acid in the resin and the organic acid.

Molding conditions for making spheres that are 1.53 inches in diameter for which data is presented in Table 7 are shown in Tables 6.

TABLE 6

Molding Conditions for Spheres

| | Temp. ° C. |
|---|---|
| Rear | 183 |
| Center | 173 |
| Front | 173 |

TABLE 6-continued

Molding Conditions for Spheres

| | |
|---|---|
| Nozzle | 177 |
| Mold Front/Back | 10 |
| Melt | 195 |
| Pressures Kg/cm² | |
| Injection 1st Stage | 130 |
| Injection 2nd Stage | 110 |
| Injection Hold | 13 |
| Cycle Times (sec) | |
| Pack | 10 |
| Hold | 480 |
| Booster | 10 |
| Cure Time | 15 |
| Screw Retraction | 5.35 |

TABLE 7

| Sample | Atti Compression | COR @ 125 FT/SEC |
|---|---|---|
| 1A | 75 | .826 |
| 2B | 75 | .826 |
| 3C | 78 | .837 |
| 4D | 76 | .837 |
| 5E | 97 | .807 |

The results show values significantly higher than 0.785 in COR and less than 100 Atti compressions. These resins can be filled with dense fillers such as zinc oxide and softened with polyetheresters such as those available from E. I. du Pont de Nemours and Company under the tradename, Hytrel® to give thermoplastic golf ball parts.

What is claimed is:

1. A composition comprising a thermoplastic polymer that is melt-processible which, when formed into a sphere that is 1.50 to 1.54 inches in diameter, has a COR (coefficient of restitution) of at least 0.785 measured by firing the sphere at an initial velocity of 125 feet/second against a steel plate positioned 3 feet from the point where initial velocity is determined and dividing the velocity of rebound from the plate by the initial velocity and an Atti compression of no more than 100 and wherein the thermoplastic polymer consists essentially of at least one of (a) E/X/Y copolymers where E is ethylene, X is a $C_3$ to $C_8$ $\alpha,\beta$ ethylenically unsaturated carboxylic acid, and Y is a softening co-monomer of the E/X/Y copolymers, wherein X is about 3–30 wt. % of the E/X/Y copolymer or partially neutralized ionomers thereof, and Y is about 0–30 wt. % of the E/X/Y copolymer; and (b) one or more aliphatic, mono-functional organic acids having fewer than 36 carbon atoms or salts thereof being present in the range of about 25 to about 150 parts per hundred parts by weight of the E/X/Y copolymer, wherein greater than 90% of all the acid of (a) and of (b) is neutralized with a cation source, wherein said thermoplastic composition is melt-processible and the melt-processibility is retained when greater than 90% of the acid of said (a) and (b) is neutralized and wherein neutralization takes place by the addition of the cation source concurrently with the melt blending of (a) and (b) or subsequently to the melt blending of (a) and (b).

2. The composition of claim 1 wherein the COR is at least 0.800.

3. The composition of claim 1 wherein the COR is at least 0.810.

4. The composition of claim 1 wherein the organic acid or salt thereof is one that is non-volatile and non-migratory.

5. The composition of claim 4 wherein X is about 4–25% of the E/X/Y copolymer and Y is about 3–25 wt. % of the E/X/Y copolymer.

6. The composition of claim 4 wherein X is about 5–20% of the E/X/Y copolymer and Y is about 10–23 wt. % of the E/X/Y copolymer.

7. The composition of claim 4 wherein X is methacrylic acid present at greater than 18 wt. % or acrylic acid present at greater than 15 wt. % and Y is not present.

8. The composition of claim 1 wherein about 100% of the acid in (a) and (b) is neutralized.

9. The composition of claim 8 wherein an amount of cation source in excess of the amount required to neutralize 100% of the acid in (a) and (b).

10. The composition of claim 1 wherein the organic acid is one or more $C_6$ to $C_{26}$ organic acids.

11. The composition of claim 10 wherein the organic acid is one or more $C_6$ to $C_{18}$ organic acids.

12. The composition of claim 11 wherein the organic acid is one or more $C_6$ to $C_{12}$ organic acids.

13. A golf ball that comprises a cover, said cover comprising the composition of claim 1.

14. A two-piece golf ball that comprises a core and a cover surrounding said core comprising the composition of claim 1.

15. A three-piece golf ball that comprises a center, said center comprising the composition of claim 1.

16. A multi-layer golf ball that comprises a core, said core comprising the composition of claim 1.

17. A one-piece golf ball comprising the composition of claim 1.

18. A multi-layered golf ball that comprises a mantle comprising the composition of claim 1.

19. A multi-layered golf ball that comprises a core, one or more intermediate layers and a cover, each comprising the composition of claim 1.

20. A process to make highly-neutralized, melt-processible ionomer comprising the steps of (c) Melt-blending (1) at least one ethylene $\alpha,\beta$ ethylenically unsaturated carboxylic acid copolymer or melt-processible ionomer thereof; and (2) sufficient non-volatile, non-migratory agent; and (d) Concurrently or subsequently adding sufficient cation source to neutralize more than 90% of all the acid moieties of the acid copolymer or ionomer thereof and, to the extent that the non-volatile, non-migratory agent contains acid moieties, the acid moieties of the non-volatile, non-migratory agent;

wherein the ethylene $\alpha,\beta$ ethylenically unsaturated carboxylic acid copolymer or melt-processible ionomer thereof consists essentially of an E/X/Y copolymers or melt-processible ionomer of the E/X/Y copolymer, where E is ethylene, X is a $C_3$ to $C_8$ $\alpha,\beta$ ethylenically unsaturated carboxylic acid, and Y is a softening co-monomer, wherein X is about 3–30 wt. % of the E/X/Y copolymer, and Y is 0 to about 30 wt. % of the E/X/Y copolymer; and wherein the non-volatile, non-migratory agent is one or more aliphatic, mono-functional organic acids having fewer than 36 carbon atoms or salts thereof wherein the aliphatic, mono-functional organic acids being present in the range of about 25 to about 150 parts per hundred parts by weight of the E/X/Y copolymer.

21. The process of claim 20 wherein about 100% of the acid moieties are neutralized.

22. The process of claim 20 wherein the amount of cation source is in excess of the amount that is required to neutralize all the acid moieties.

* * * * *